United States Patent
DeWoskin et al.

(10) Patent No.: US 6,498,141 B2
(45) Date of Patent: Dec. 24, 2002

(54) METHOD AND APPARATUS FOR PREPARING AN ACELLULAR RED BLOOD CELL SUBSTITUTE

(75) Inventors: Richard E. DeWoskin, St. Charles, IL (US); Marc D. Doubleday, Cary, IL (US)

(73) Assignee: Northfield Laboratories, Inc., Evanston, IL (US)

( * ) Notice: Subject to any disclaimer, the term of this patent is extended or adjusted under 35 U.S.C. 154(b) by 0 days.

(21) Appl. No.: 09/155,419

(22) PCT Filed: Mar. 27, 1997

(86) PCT No.: PCT/US97/05088
§ 371 (c)(1),
(2), (4) Date: May 10, 1999

(87) PCT Pub. No.: WO97/35883
PCT Pub. Date: Oct. 2, 1997

(65) Prior Publication Data
US 2002/0025343 A1 Feb. 28, 2002

Related U.S. Application Data
(60) Provisional application No. 60/014,389, filed on Mar. 28, 1996.

(51) Int. Cl.[7] .................. A61K 38/16; A61K 35/14; C07K 14/805

(52) U.S. Cl. .................. 514/6; 514/832; 530/385; 530/402; 530/412; 530/414; 530/418; 530/427; 530/829; 424/529; 424/533

(58) Field of Search ............. 514/6, 832; 530/385, 530/402, 412, 414, 418, 427, 829; 424/529, 533

(56) References Cited

U.S. PATENT DOCUMENTS

| | | | | |
|---|---|---|---|---|
| 4,826,811 A | * | 5/1989 | Sehgal et al. | 514/6 |
| 5,194,590 A | * | 3/1993 | Sehgal et al. | 530/385 |
| 5,380,824 A | * | 1/1995 | Marschall et al. | 530/385 |
| 5,464,814 A | * | 11/1995 | Sehgal et al. | 514/6 |
| 5,789,376 A | * | 8/1998 | Hsia | 514/6 |
| 5,998,361 A | * | 12/1999 | Bucci et al. | 514/2 |

FOREIGN PATENT DOCUMENTS

EP 0 361 720 A 4/1990

* cited by examiner

Primary Examiner—Christopher S. F. Low
Assistant Examiner—Abdel A. Mohamed
(74) Attorney, Agent, or Firm—McDonnell Boehnen Hulbert & Berghoff

(57) ABSTRACT

A process is disclosed for the preparation of an essentially tetramer-free, substantially stroma-free, polymerized, pyridoxylated hemoglobin. Also disclosed is an essentially tetramer-free, substantially stroma-free, polymerized, pyridoxylated hemoglobin product capable of being infused into human patients in an amount of up to about 5 liters.

20 Claims, 6 Drawing Sheets

METHOD AND APPARATUS FOR PREPARING AN ACELLULAR RED BLOOD CELL SUBSTITUTE

This application claim benefit to Provisional No. 60/014,389 filed Mar. 28, 1996.

BACKGROUND OF THE INVENTION

1. Field of the Invention

This invention relates to methods and apparatus for preparing red blood cell substitute products, i.e., hemoglobin products. It further relates to an acellular red blood cell substitute comprising an essentially tetramer-free, cross linked, polymerized, pyridoxylated hemoglobin solution which is free of stromal contaminants.

2. Description of Related Art

For a number of years, blood banks have provided whole blood for replacement during surgery, because of trauma, or for other situations. However, whole blood obtained from human donors is not suitable for a variety of uses. In particular, the use of whole blood is problematic because of the requirement for donor-typing, stability and shelf-life problems and toxicity caused by viruses and other contaminants. These problems are especially pertinent to emergency situations, such as the use of blood by the military. Consequently, much effort has been devoted to the development of substitutes for whole blood obtained from human donors. This development has resulted in various modifications to blood from human or other mammalian sources. Stroma-free hemoglobin is known in the art to have oxygen transport and reversible oxygen (or ligand) binding capacities. Since toxicity problems have precluded use as a blood substitute, stroma-free hemoglobin has required further modifications to provide a nontoxic, useful pharmaceutical product.

These modifications include (1) rendering hemoglobin free or substantially free of stroma and stromal contaminants; (2) pyridoxylation; (3) polymerization or crosslinking; (4) removal of tetramer, and (5) modification with carbon monoxide or other ligands.

However, hemoglobin solutions prepared by these techniques, while capable of carrying sufficient quantities of oxygen to support life, have been plagued with many undesirable side effects and properties. For example, a major troubling side effect is a decrease in kidney performance. These changes were thought to be due to the presence of unwanted contaminants such as bacterial endotoxin or fragments of red cell membranes (stroma). While contaminants such as these can indeed produce renal alterations, hemoglobin solutions essentially free of the above contaminants still produce substantial renal dysfunction. The cause for the renal dysfunction has been ascribed to physiologically unacceptable amounts of unpolymerized hemoglobin tetramer. Other undesirable side effects of the infusion of tetrameric hemoglobin are vasoconstriction, hemoglobinuria, depression of heart rate, elevation of mean arterial blood pressure and extravasation of infusate especially into the peritoneal cavity.

In practice, no known hemoglobin-derived blood substitute has been successful in totally avoiding toxicity problems. These products also have unacceptably low half-lives after administration to human patients. Such half-lives require replacement of blood volume repeatedly over short periods of time. Consequently, there is a substantial need for hemoglobin products that are non-toxic to patients and have substantial half-lives after administration. Of course, these products must be capable of reversibly transporting oxygen to tissues in a manner similar to that achieved by whole blood.

SUMMARY OF THE INVENTION

The present invention provides hemoglobin substitutes that are non-toxic to humans and have substantial half-lives of at least 15 hours when administered to humans. The hemoglobin products of the invention are stroma-free, pyridoxylated and polymerized as well as being free of viral and other toxic contaminants. Further, these products are substantially free of leukocytes (white blood cells) and platelets.

The present invention also encompasses processes for preparing the inventive hemoglobin substitutes. The processes include removing leukocytes and platelets from blood; washing and lysing the red blood cells; removing stromal contaminants and stroma by filtration and heat-treating; preparing the deoxy form of the hemoglobin; pyridoxylation and polymerization; further purification and concentration; and deoxygenation. The resulting hemoglobin product may be then formulated to provide a hemoglobin product having levels of various electrolytes within normal physiological ranges.

The invention also provides an aqueous formulation of pyridoxylated, polymerized hemoglobin, where the hemoglobin is a glutaraldehyde-polymerized hemoglobin containing tetrameric material, having the molecular weight profile of FIG. 3. This formulation may be used to prepare an acellular red blood cell substitute. In this aspect, the formulation is first purified to remove tetramer and then combined with appropriate amounts of electrolytes to produce a physiologically acceptable, acellular, red blood cell substitute that may subsequently be used to treat a human patient requiring an infusion of an oxygen carrier.

DETAILED DESCRIPTION OF THE PREFERRED EMBODIMENT

Figure 1:
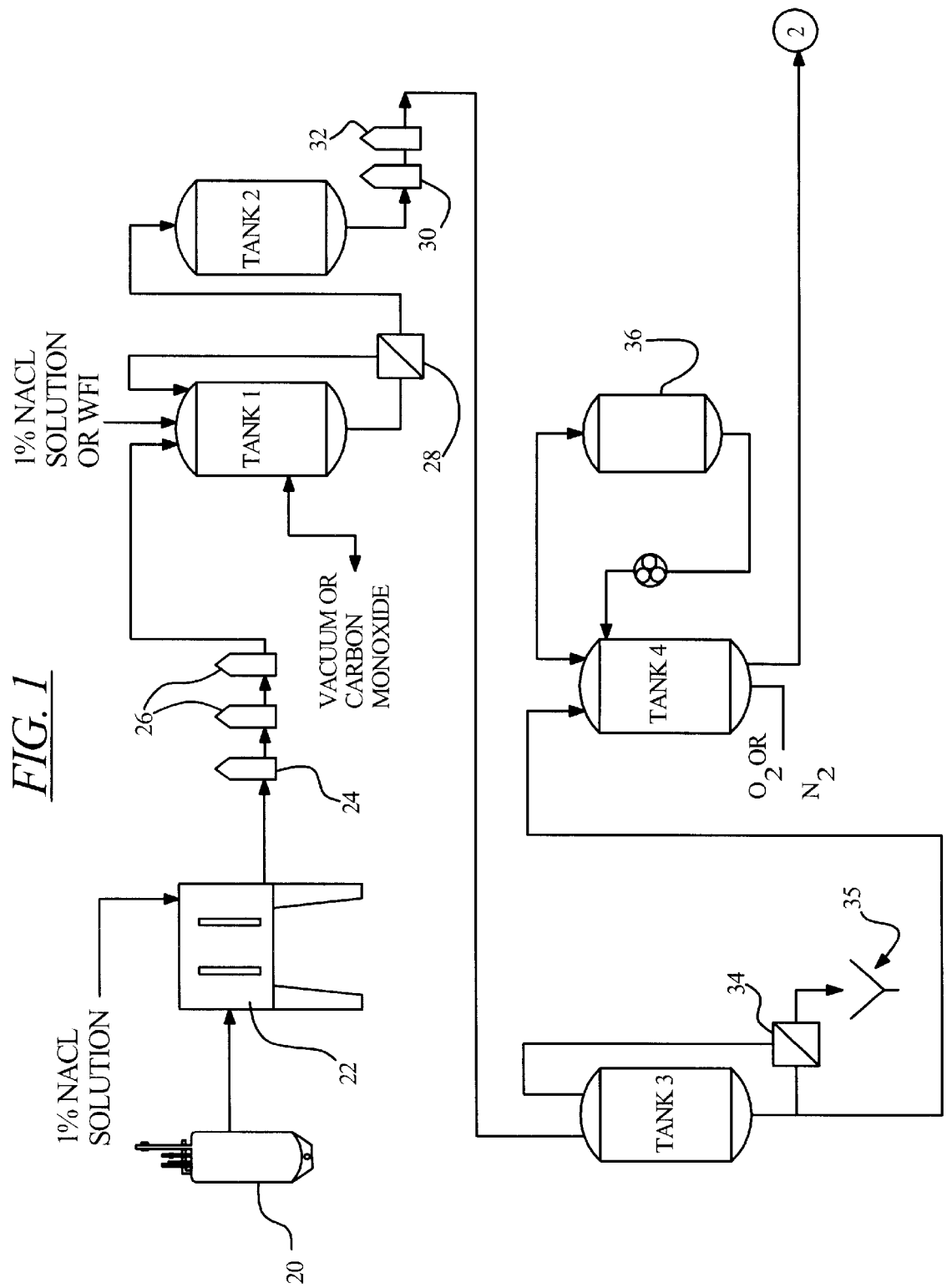
FIG. 1 is a schematic diagram depicting the portion of the process and equipment used to result in a deoxygenated hemoglobin solution prepared for pyridoxylation and polymerization.

The present invention concerns an acellular red blood cell substitute comprising an essentially tetramer-free, crosslinked, polymerized, pyridoxylated hemoglobin which is substantially free of stroma, stromal contaminants and other contaminants.

As used herein, the term "cross-linked" means the chemical emplacement of molecular "bridges" onto or into a molecule, or between molecules with the purpose of altering the shape, size, function or physical characteristics of the molecule. Cross-linked molecules may be polymerized or non-polymerized, i.e., cross-linked molecules may be tetrameric.

As used herein, the term "tetramer" refers to hemoglobin molecules having a molecular weight of about 64 Kd; that is, the term refers to both native and intramolecularly crosslinked hemoglobin molecules.

As used herein, the term "essentially tetramer free" denotes the level of purity with respect to tetramer contamination at which certain biological responses to tetramer administered into a mammal are no longer present. A main criterion is the absence of alterations in renal function when pharmaceutically effective amounts are infused, that is, at a level of purity of about 99% or better (less than about 1% of tetramer is present). The preferred product produced by the inventive process contains no more than about 0.8% tetramer based on the weight of total hemoglobin (THb). In other words, an essentially tetramer-free product according to the invention contains no more then physiologically acceptable amounts of unpolymerized hemoglobin tetramer. Particularly preferred products of the invention contain less than about 0.5% tetramer; the most particularly preferred products of the invention contain about 0.3–0.4% tetramer. Such amounts of tetramer have been found to be physiologically acceptable.

As used herein, the terms "ultrapurified product" or "purified product" have the same meaning as the term "essentially tetramer-free."

As used herein, % total hemoglobin (THb) is defined as grams of hemoglobin/100 mL of solution.

As used herein, the term "polymerizing solution" means a solution containing a "cross-linking" or polymerizing agent, such as glutaraldehyde, imido esters, diaspirin or others, in a biochemically suitable carrier.

As used herein, the term polymerized means the placement of molecular bridges between molecules or tetrameric submits where the size and weight of the resulting polymerized molecule is increased with respect to native or tetrameric hemoglobin. Polymerized hemoglobin is not tetrameric hemoglobin.

By a solution of hemoglobin as used herein is meant a solution of tetrameric hemoglobin or polymerized hemoglobin molecules where the molecules are not contained within a red blood cell. Such a solution need not be free of or substantially free of red blood cell stroma or stromal contaminants. However, preferred polymerized hemoglobin solutions are free of red blood cell stroma and stromal contaminants.

By the term "semipermeable membrane" is meant a membrane permeable to some molecular species and not to others and, i.e., a membrane which acts as a selective filter excluding certain molecular weights.

The product of the process according to the present invention, a polymerized, pyridoxylated, hemoglobin solution essentially free of tetrameric (native or intramolecularly crosslinked) hemoglobin, stromal and various other contaminants, produced from heat treated, virally inactivated tetrameric hemoglobin, is physiologically acceptable as well as therapeutically and clinically useful. The product has reversible oxygen binding capacity which is necessary for oxygen transport properties. Most notably, the product demonstrates good loading and unloading characteristics in usage which correlates to having an oxygen-hemoglobin dissociation curve ($P_{50}$) similar to whole blood. The product binds oxygen with high affinity in the capillaries through the lungs and then adequately releases oxygen to the tissues in the body. The product also does not require compatibility studies with the recipient.

The product also has a half-life when administered to humans of about at least 15 hours and more preferably of about 24 hours. This hemoglobin product may be infused into patients in amounts of up to about 3.0 L and even up to about 5.0 L. In other words, the inventive hemoglobin product can be used to replenish essentially all of a human patient's blood volume without causing vasoconstriction, renal toxicity, hemoglobinuria or other problems associated with intravenous administration of synthetic or semisynthetic oxygen carriers and blood substitutes. Thus, the invention includes a method of transfusing a patient, preferably a human patient, with an amount of a stroma-free, tetramer-free, polymerized, pyridoxylated hemoglobin product that is non-toxic to the patient, where the amount is up to at least about 5.0 L. Such a method includes attaching the patient or subject to an infusion device or other such equipment for infusing or transfusing the patient.

The process of this invention is unique in that it yields a product having a level of tetramer of no more than about 1% and, more preferably, no more than about 0.8% by weight based on the weight of total hemoglobin in the solution. The process of this invention provides a further advantage in that it can render the final product substantially free of microbial and viral antigens and pathogens. Such microbial and viral antigens and pathogens are reduced to nondetectable levels i.e. The product is sterile as determined by the analysis set forth in the United States Pharmacopoeia, XXII Chapter <71>. Examples of such antigens and pathogens include, for example, bacterial, rickettsial, fungal, protozoan, viral and other organisms. Most importantly, the process provides a biological product free of viruses that cause hepatitis and acquired immune deficiency syndrome (AIDS).

Insofar as the physiological properties are concerned, the biological product of this invention, when infused in amounts of up to at least, about 5.0 L, does not cause vasoconstriction, renal toxicity, hemoglobinuria and other problems implicated with intravenous administration of known hemoglobin solutions containing physiologically undesirable amounts of tetrameric hemoglobin. Intravenous administration of the product produced by the process described herein results in no appreciable decrease in urine production, no appreciable decrease in glomerular filtration rate, no appreciable extravasation into the peritoneal cavity and no appreciable change in the color of urine produced.

Therefore, the process of the invention provides an acellular red blood cell substitute useful in the treatment of trauma, myocardial infarction, stroke, acute anemia and oxygen deficiency disorders such as hypoxemia, hypoxia or end stage hypoxia due to impairment or failure of the lung to fully oxygenate blood. The product also is useful in the treatment of any disease or medical condition requiring a resuscitative fluid (e. trauma, specifically hemorrhagic shock), intravascular volume expander or exchange transfusion. In addition to medical treatment, the product can be useful in preserving organs for transplants.

The inventive process comprises the following procedures:

1. red cell aspiration and filtration
2. cell wash/lyse
3. heat treatment
4. ultrafiltration concentration
5. degassification
6. chemical modification
7. purification
8. UP poly concentration
9. deoxygenation
10. formulation The preferred starting material in the process of the present invention is outdated whole human blood or packed red blood cells. In addition, non-outdated blood (indated) may also be used. Preferably, whole blood is not used in this process if it has been in storage for more than 2 weeks past the expiration date indicated on the bag. The use of whole blood outdated by more than 2 weeks provides additional difficulty in extracting the hemoglobin and removing cellular remnants such as stromal proteins and contaminants.

All processes described herein are applicable to other mammalian blood with possible minor modifications within the skill of the art. Most of the process may be carried out at about 2° C. to about 80° C., preferably about 4° C.

During red cell aspiration and filtration, the red blood cells (RBC) are aseptically extracted from donor bags without introducing air into the blood and passed across a series of filters to result in a RBC suspension having reduced amounts of leukocytes and platelets. The resulting suspension is then subjected to cell washing/lysing.

The suspension is washed under carbon monoxide atmosphere with an about 1% NaCl solution to remove residual plasma proteins. The washed RBC are then treated with water for injection (WFI) to lyse the cells and the resulting mixture clarified using a cross flow filtration unit. The clarified product is then heat-treated to precipitate additional stromal material which is removed by filtration. The product of this procedure is a stroma-free hemoglobin (SFH) solution with a THb of about 3% (w/v).

The heat treated and stroma-free hemoglobin solution containing carboxyhemoglobin is concentrated and degassed to yield a SFH solution containing deoxyhemoglobin. Degassification involves first saturating the carboxyhemoglobin solution with oxygen for about 16 hours to yield a solution of oxygenated hemoglobin and about 7% by weight, based on the total weight of hemoglobin, of carboxyhemoglobin. Subsequently, the oxygen is driven off with nitrogen, argon or helium to form a solution containing free hemoglobin, i.e., uncomplexed hemoglobin, and about 7% by weight, based on the total weight of hemoglobin, of oxyhemoglobin. The resulting degassed solution is filtered and transferred into a vessel for chemical modification.

Subsequent to degassification, the stroma-free hemoglobin solution is pyridoxylated using pyridoxal-5'-phosphate (P5P) at a molar ratio of pyridoxal-5'-phosphate to hemoglobin of about 1:1 to 3:1. Alternatively, the stroma-free hemoglobin may be pyridoxylated using 2-Nor-2 formyl pyridoxal-5'-phosphate. A reducing agent such as sodium cyanoborohydride or preferably sodium borohydride is added to the pyridoxylation mixture. Excess reagents and salts are removed by dialysis against pyrogen free water or, preferably, diafiltration with WFI. The pyridoxylated hemoglobin is then polymerized with a glutaraldehyde solution.

The stroma-free, pyridoxylated hemoglobin solution is polymerized using an aqueous glutaraldehyde solution. The duration of polymerization and the amount of glutaraldehyde added is dependent on volume of the hemoglobin solution, the desired yield of polymers and the desired molecular weight distribution. In general, longer polymerization times increase the yield and the molecular weight distribution of the polymers. A yield of approximately 75% by weight of polymers, based on the total weight of hemoglobin, is obtained in about 16–18 hours. The preferred end point of the polymerization is defined as that point where the solution contains about 75% by weight of polymers, based on the total hemoglobin weight, as monitored by size-exclusion HPLC. Alternatively, the endpoint is defined as the point at which the solution contains about 65% of polymers based on the total weight of hemoglobin, i.e., about 2.5 hours.

The polymerization reaction is quenched by the addition of aqueous glycine. The buffer must be added as quickly as possible. The cross-links are then stabilized by adding, again as quickly as possible, a solution of aqueous sodium borohydride. This polymerized solution is subsequently concentrated and then diafiltered under an atmosphere of oxygen to oxygenate the solution. Water is finally added to the solution until the solution contains about 4% by weight hemoglobin.

Figure 3:
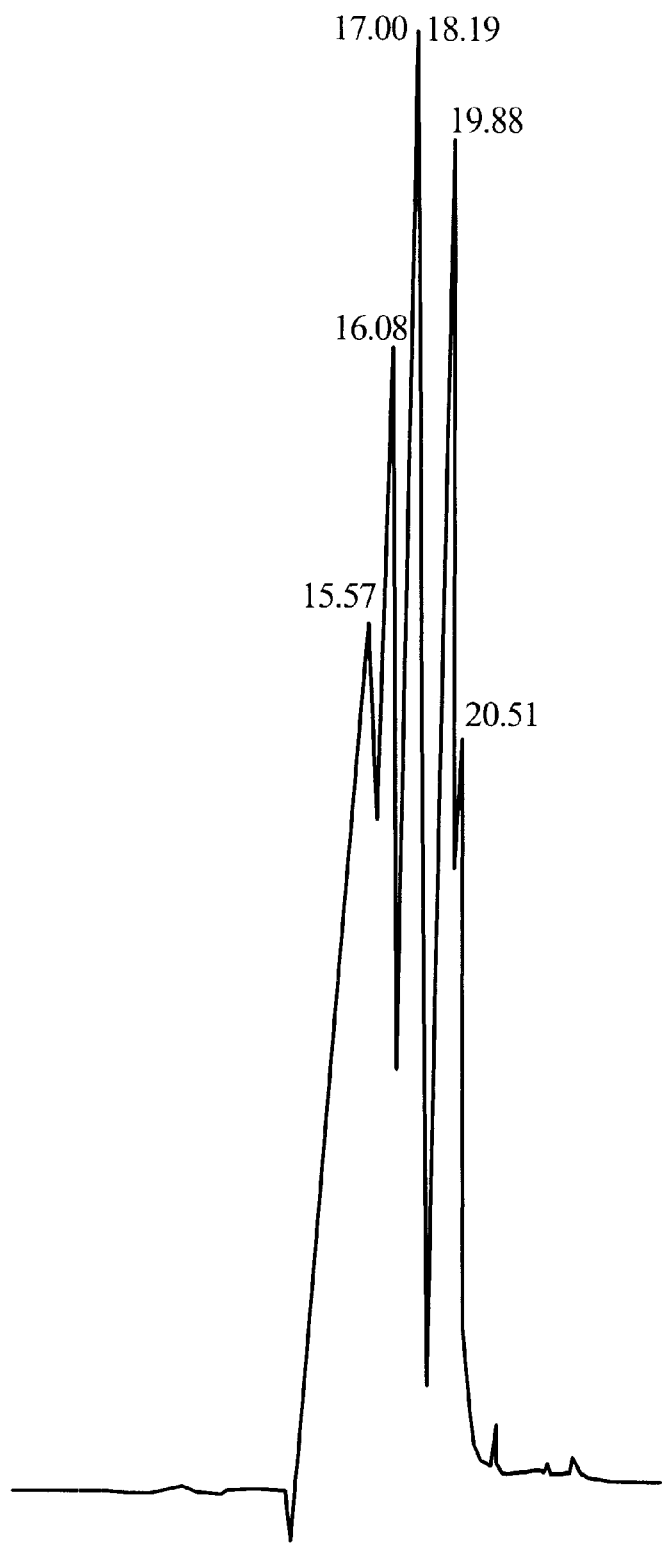
FIG. 3 is an HPLC tracing of polymerized material after glycine treatment prior to purification. Polymerized product is indicated by peaks at retention times (RT) 15.57, 16.08, 17.00, and 18.19. Tetramic material is indicated by peaks at RT 19.88 and 20.51. Polymer is 76.2% of this material.
Figure 4:
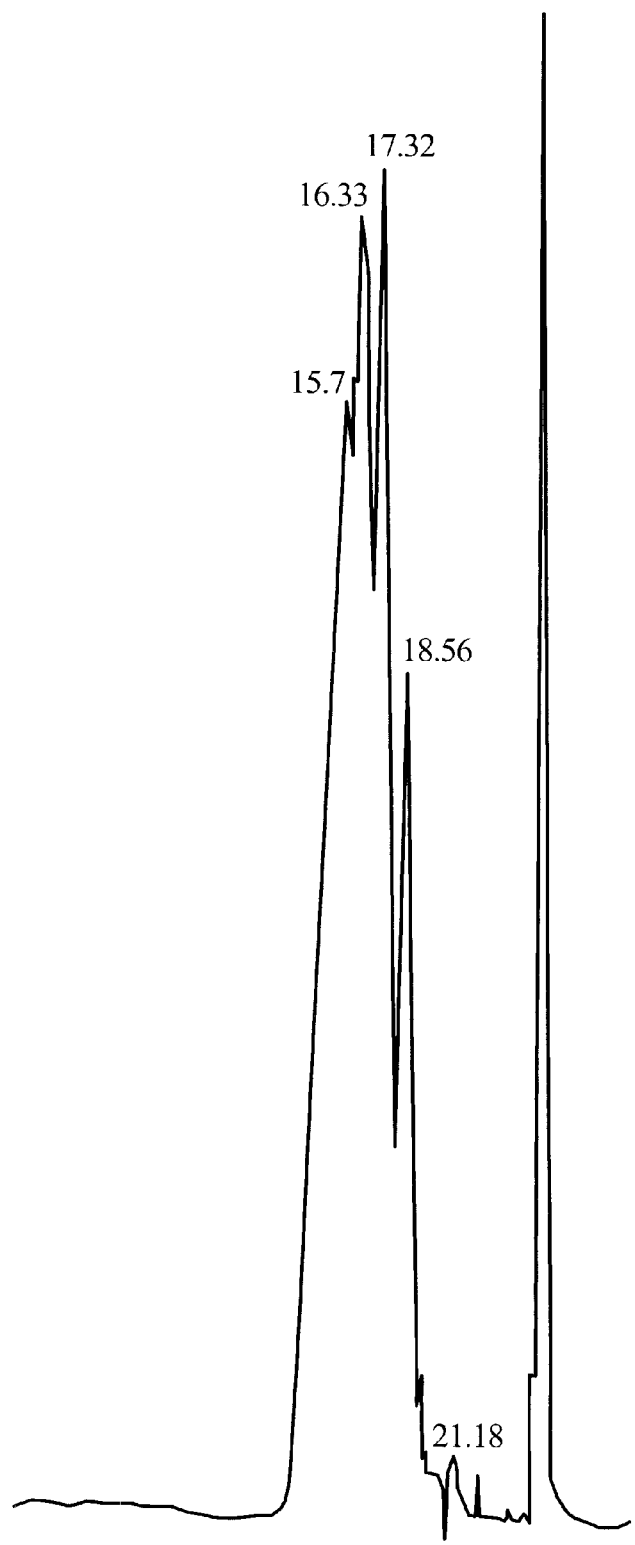
FIG. 4 is an HPLC tracing of the hemoglobin product of the invention. Polymerized hemoglobin is indicated by the peaks at RT 15.7, 16.33, 17.32, and 18.56. Tetramer is indicated by the peak at RT 21.18.

Polymerization according to the invention results in a high yield of polymers having a narrow molecular weight range as shown in FIG. 3 and Example 1 below.

The polymerized, pyridoxylated hemoglobin solution is then purified by column chromatography, filtration, e.g., membrane filtration, or both, to remove residual unpolymerized (tetrameric) hemoglobin from the solution. The purified polymerized hemoglobin solution is then concentrated to about 6% using an ultrafiltration apparatus in preparation for gas exchange.

The concentrated solution is then deoxygenated with nitrogen. The deoxygenation takes place at about 10–12° C. until the amount of oxyhemoglobin in the solution is less than about 16% by weight of the total hemoglobin.

The resulting deoxygenated, purified, and polymerized hemoglobin solution is then concentrated by ultrafiltration under a nitrogen atmosphere in a cooled vessel. The pH is adjusted to about 8.8–9.0, and the amounts of electrolytes may be adjusted as necessary to levels representing that of normal plasma. In addition, conventional antioxidants such as glutathione, ascorbate or glucose may also be optionally added. After the solution is concentrated to the desired level, preferably about 10% by weight polymerized, pyridoxylated, purified, tetramer-free, stroma-free hemoglobin, the solution is sterilized by filtration and transferred via a sterile transfer apparatus into suitable pharmaceutically acceptable containers.

The characteristics of the resulting hemoglobin solution are shown below:

|  | Polymerized Hemoglobin |
| --- | --- |
| Total Hemoglobin (g/dl)[1] | 9.5–12.0 |
| Methemoglobin (% of total Hb)[1] | <8.0 |
| Carboxyhemoglobin (% of total Hb)[1] | <5.0 |
| $P_{50}$ (torr)[1] | 23–32 |
| Osmolality (mmol/Kg)[2] | 280–360 |
| Sodium (mmol/L)[3] | 135–155 |
| Potassium (mmol/L)[3] | 3.5–4.5 |
| Chloride (mmol/L)[3] | 85–110 |
| Free Iron (ppm)[4] | <2.0 |
| Molecular Wt. Dist. - 128 Kd peak (%)[5] | 10–24 |
| Molecular Wt. Dist. - 192 Kd peak (%)[5] | 18–30 |
| Molecular Wt. Dist. - 256 Kd peak (%)[5] | 45–70 |
| Tetramer (64K)(%)[5] | <0.8 |
| Endotoxin (EU/mL)[6] | <0.03 |

-continued

| | Polymerized Hemoglobin |
|---|---|
| Phospholipids ng/Hb[7] | <50 |
| Glycolipids (ng/Hb)[7] | <2 |

[1]Level in polymerized hemoglobin determined spectrophotometrically.
[2]Level in polymerized hemoglobin determined by osmometry.
[3]Level in polymerized hemoglobin determined by ion specific electrode.
[4]Level in polymerized hemoglobin determined by atomic absorption.
[5]Determined by size exclusion-HPLC.
[6]Determined by LAL using an assay commercially available from Associates of Cape Cod, assay components have catalog nos. 100-5, 800-1, and 3100-5.
[7]Determined by HPTLC The following examples demonstrate certain aspects of the present invention. However, it is to be understood that these examples are for illustrative purposes only and do not purport to be wholly definitive as to conditions and scope of this invention. All temperatures are expressed in degrees Celsius unless otherwise specified. Unless otherwise noted, all percentages, e.g., of total hemoglobin (THb), are expressed as weight/volume (w/v). It also should be appreciated that when typical reaction conditions (e.g., temperature, reaction times) have been given, the conditions which are both above and below these specific ranges can also be used, though generally less conveniently.

Unless noted to the contrary, all vessels and tanks used in the inventive process are made of 316-L Stainless Steel, preferably a pharmaceutical grade of such stainless steel that has been highly polished and therefore easily and rapidly cleaned. The various connecting pipes and tubes are made of the same stainless steel or of a pharmaceutical grade Teflon or silicone tubing. The filters and membranes used in the process may be purchased from Millipore Inc., Pall-Filtron, or Cuno Inc.

The half-life of the resulting product of the invention is determined in vio in mammals, e.g., humans. Typically, a blood sample is removed from the mammal a period of time after the mammal has been infused with the product. The amount of the product is then determined by centrifuging the blood sample, expressing the plasma portion, determining plasma hemoglobin levels spectrophotometrically, and then correlating the amount of product remaining in the mammal to the half-life of the product.

Size Exclusion Chromatography HPLC according to the invention is carried out as follows:

The sample is diluted with 0.2 M pH 6.9 potassium phosphate buffer to 0.2 g/dl, filtered through a 0.2 $\mu$ filter and injected into an HPLC system consisting of the following components (in order of system flow):
1. Pharmacia model 2248 pump
   mobile phase is 0.2 M pH 6.9 potassium phosphate
   flow rate is 1.0 mL/minute
2. 45 cm PEEK or titanium tubing, 0.010 in. I.D.
3. Rheodyne model 7725i injector with 200 $\mu$L PEEK sample loop
4. 18 cm PEEK or titanium tubing, 0.010 in. I.D.
5. Upchurch model A431 0.5 $\mu$ filter
6. 9 cm PEEK or titanium tubing, 0.010 in. I.D.
7. Phenomenex Biosep SEC S-3000 75×7.8 mm Guard column
8. 24 cm PEEK or titanium tubing, 0.010 in. ID.
9. Phenomenex Biosep SEC S-3000 600×7.8 mm Analytical column
10. 23 cm PEEK or titanium tubing, 0.010 in. I.D.
11. Pharmacia Uvicord SD UV detector
    wavelength: 280 um
    flow cell: 8 $\mu$L vol., 2.5 mm pathlength
    range: 2 AUFS
    time constant: 10 seconds The peak absorbance at 280 nm is recorded by a LKB 2221 Integrator, which integrates the individual peak areas and calculates the total Hemoglobin area for each polymeric species.

A further understanding of the invention may be obtained from the following nonlimiting examples.

EXAMPLE 1

Referring now to FIG. 1, donor bags 20 of outdated blood (whole blood or packed red blood cells) are situated in a suitable aseptic aspiration apparatus 22. As an example of a suitable aspiration apparatus is a system having two aspiration stations. Once a donor bag is placed in the aspiration station, a needle in the aspiration apparatus punctures the donor bag, introduces about 150 ml of a 1% (w/v) aqueous sodium chloride solution and aspirates the outdated blood from the donor bag under reduced pressure or vacuum. The aspirated blood is passed through a 100 $\mu$ depth filter 24 and subsequently through two 5 $\mu$ depth 26 filters in series. As the blood passes through the 5 $\mu$ depth filters, leukocytes are removed from the blood. Typically, about 170 units of outdated whole blood are aspirated, filtered and subsequently transferred to Tank 1 as shown in FIG. 1. The filters are then rinsed with about 75 liters of a 1% (w/v) aqueous sodium chloride solution.

Prior to the introduction of the blood into Tank 1, Tank 1 is charged with about 70 L of a 1% aqueous sodium chloride solution. After all 170 units of outdated whole blood have been aspirated, filtered and transferred, and the filters have been rinsed, the tank contains about 250 liters of a 4% total hemoglobin solution. During the aspiration and filtering steps, Tank 1 is maintained at a reduced pressure, i.e., a vacuum of 20–28' Hg. Once all the outdated blood has been transferred to Tank 1, the vacuum is switched off and carbon monoxide is introduced into the tank so that the tank contains an atmosphere of carbon monoxide.

Tank 1 is coupled to a 0.65 $\mu$ tangential flow filter 28 as shown in FIG. 1. The initial charge of 250 liters of 4% total hemoglobin solution is concentrated to approximately 125 L of an 8% total hemoglobin solution by microfiltration through the tangential flow filter. The pH of the hemoglobin solution at this point is about 6 to 6.5. Subsequent to concentrating to 8% total hemoglobin, the solution is washed by adding a 1% (w/v) sodium chloride solution, diafiltering and removing the filtrate at the same rate sodium chloride solution is added. The 125 L of hemoglobin solution is typically washed with about 8 volumes of the 1% sodium chloride solution (about 1,000 L). Subsequent to washing, the solution is concentrated to about 70 L, i.e., about 14% total hemoglobin, and "water for injection" (WFI) is added to bring the volume of the solution up to about 180 L. With the addition of the WFI, the cells swell and rupture releasing hemoglobin into solution. The concentration of the resulting hemoglobin solution is about 5% total hemoglobin (THb).

The resulting solution is clarified while still in Tank 1. The solution is first concentrated to about 50 L and the filtrate transferred to Tank 2. As the solution is pumped across the filter, red blood cells stroma contaminants and cell wall material is retained and removed by the filter. The remaining 50 L of solution in Tank 1 is washed (diafiltered) with about 2.5 volumes of WFI. This 2.5 volumes of wash is added to Tank 2. The material remaining in Tank 1 is then concentrated to about 20 L and the filtrate added to Tank 2. The volume resulting in Tank 2 is about 280 L of a 3.3% total hemoglobin solution.

The resulting solution of stroma-free hemoglobin is then heat treated in Tank 2 at a temperature of about 60–62° C. over a period of about 10 hours. During this time, the solution is moderately agitated. As the solution is heated and passes a temperature of about 55° C., a precipitate forms.

The resulting 3.3% THb (w/v) stroma-free, heat treated hemoglobin solution is then filtered through a 0.2 $\mu$ filter 30 followed by a 0.1 $\mu$ 32 filter and transferred to Tank 3. The filtered hemoglobin solution is then concentrated to about 18% THb and subsequently washed and diafiltered with 4 volumes of WFI (180 L). The concentration and diafiltration is accomplished using a 10 kilodalton (kd) molecular weight ultrafilter 34. Drain 35 associated with ultrafilter 34 collects filtrate. At this point, the 45 L of 18% total hemoglobin solution contains less than 50 ng of phospholipid per gram of hemoglobin, less than 2 ng of glycolipid per gram of hemoglobin, less than 1% methemoglobin, less than about 0.03 endotoxin units of endotoxin per milliliter at a pH of about 6 to 6.5. This hemoglobin in the solution is carboxyhemoglobin.

The resulting carboxy hemoglobin solution is then transferred to Tank 4 where the carboxyhemoglobin is first oxygenated and then deoxygenated. Tank 4 is fitted with a gas sparge ring coupled to oxygen and nitrogen gas lines, a feed from the tank bottom to a metered spray apparatus positioned at the top of Tank 4, and a foam overflow collector connected to Foam Can 1 such that foam generated in Tank 4 is fed into Foam Can 36 where the foam condenses into liquid and is fed back into Tank 4. Tank 4 further includes a set of Pall Rings filling approximately one-third of the tank volume. Foam Can 36 includes a gas vent for removal of gas. The solution in Tank 4 is a 13% total hemoglobin solution.

During a first oxygenation step, oxygen is sparged through the solution at a rate sufficient to have uniform dispersion of gas in the vessel. The vessel, 200 L in volume, is sparged at a rate of about 25 L/min. with gas. Oxygenation of the carboxyhemoglobin is conducted for a period of about 16 hours such that the resulting solution contains less than 5% carboxyhemoglobin based on the weight of total hemoglobin. Oxygenation is conducted at a temperature of about 10° C. The foam generated in Tank 4 is collected in Foam Can 36 and after settling, the resulting solution is transferred back into Tank 4.

After oxygenation, the solution is sparged with a similar flow of nitrogen for about 6 hours or until less than 10% oxyhemoglobin based on the weight of total hemoglobin remains in the solution. The nitrogen sparge is conducted at a temperature of about 10° C. and a pH of about 6 to 6.5. Alternatively, carboxyhemoglobin could be converted to deoxyhemoglobin using a membrane exchanger. It is noted that there is substantially no denaturing of the hemoglobin as would normally be expected from the foaming step. The resulting deoxygenated solution is now prepared for chemical modification.

Figure 2:
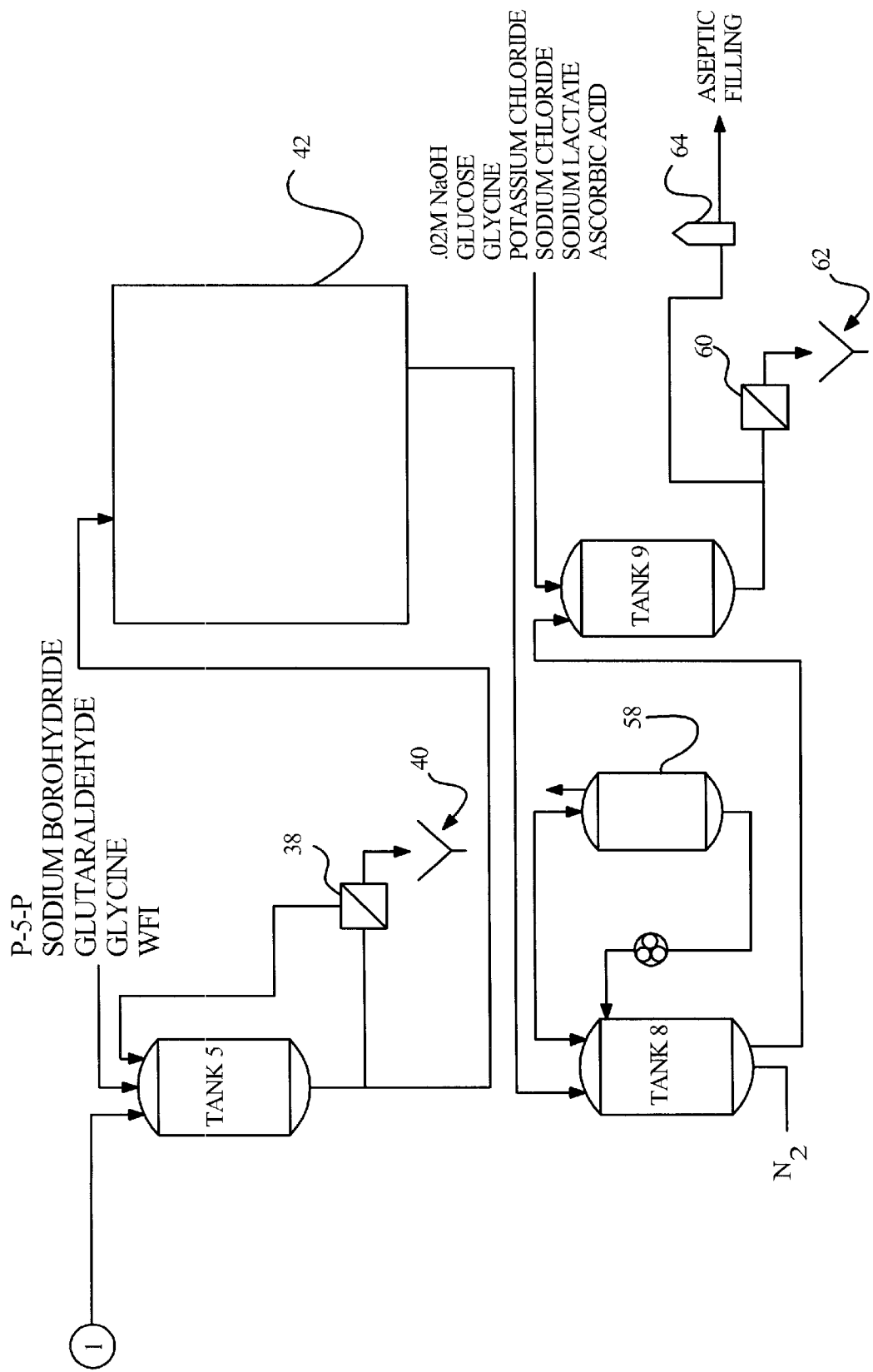
FIG. 2 is a schematic diagram depicting the portion of the process and apparatus beginning with pyridoxylation and polymerization and resulting in a deoxygenated, purified, pyridoxylated, polymerized hemoglobin product and the portion of the process and apparatus used to formulate the final hemoglobin product having physiological levels of electrolytes.

Referring now to FIG. 2, the deoxyhemoglobin solution is transferred to Tank 5 for chemical modification. To Tank 5 containing the deoxyhemoglobin at about 4° C. solution is then added an aqueous solution of pyridoxyl-5-phosphate (P5P) (93.75 g/L) at a 1:1 to 3:1 P5P to hemoglobin molar ratio. A 2:1 molar ratio of P5P to hemoglobin is preferred. The pyridoxylation is conducted at a temperature of about 4° C. The P5P solution is typically added over about 1 minute and mixed for approximately 15 minutes, after which a sodium borohydridelsodium hydroxide solution is added to the hemoglobin solution at a molar ratio of sodium borohydride to hemoglobin of about 20:1. A suitable aqueous sodium borohydride/sodium hydroxide solution contains 0.8 g of sodium hydroxide per 2 liters and 90.8 g of sodium borohydride per 2 liters. The borohydride solution is added as rapidly as possible over a period of about 1 minute and then stirred for one hour. The resulting 50 L solution of pyridoxylated hemoglobin is subsequently diafiltered using 10K Dalton ultrafilter 38 to remove excess reactants with 4 volumes of WFI. Drain 40 associated with ultrafilter 38 collects the filtrate from filter 38.

After diafiltration with 4 volumes, i.e., 200 L, of WFI, the hemoglobin is polymerized. To Tank 5 containing the pyridoxylated hemoglobin is added sufficient WFI to prepare a 4.5% total hemoglobin solution (about 175 L of hemoglobin solution). A glutaraldehyde solution is added to the pyridoxylated hemoglobin solution at a molar ratio of glutaraldehyde to hemoglobin of about 24:1. The glutaraldehyde solution is typically added over a period of about 2.5 hours by metering pump to the hemoglobin solution. The polymerization reaction is allowed to proceed for about 18 hours. The target molecular weight distribution is about 75% polymer and 25% tetramer. The target polymers have molecular weights of less th about 600,000 with a predominant fraction of the molecular weights residing in the 100,000–350,000 range.

When the polymerization reaction reaches the target molecular weight distribution (after about 18 hours), aqueous glycine (about 166 g/L) is added (as a quench) to the hemoglobin solution at a 140:1 molar ratio of glycine to hemoglobin. See FIG. 3 which is an HPLC tracing of the resulting polymerized, glycine-quenched hemoglobin product. The resulting solution is then mixed for about 10 minutes after which a sodium borohydride sodium/hydroxide solution (having the concentration identified above) is added to the hemoglobin solution at a 28:1 molar ratio of sodium borohydride to hemoglobin. This resulting mixture is stirred for about 1 hour. The solution is then concentrated to about 50 L (ultrafilter 38) and washed with 4 volumes (200 L) of WFI. An additional aliquot of sodium borohydride at the same molar ratio as indicated above is added to the concentrated solution and again mixed for 1 hour. The resulting solution is washed with 4 volumes of WFI (200 L) resulting in polymerized, pyridoxylated, stroma-free hemoglobin that has been heat treated.

The resulting solution is oxygenated by allowing the solution to stand under an oxygen atmosphere and is subsequently transferred to a purification system 42. The purification may be achieved by column chromatography, filtration, preferably membrane filtration (diafiltration), or a combination of filtration and column chromatography.

Figure 5:
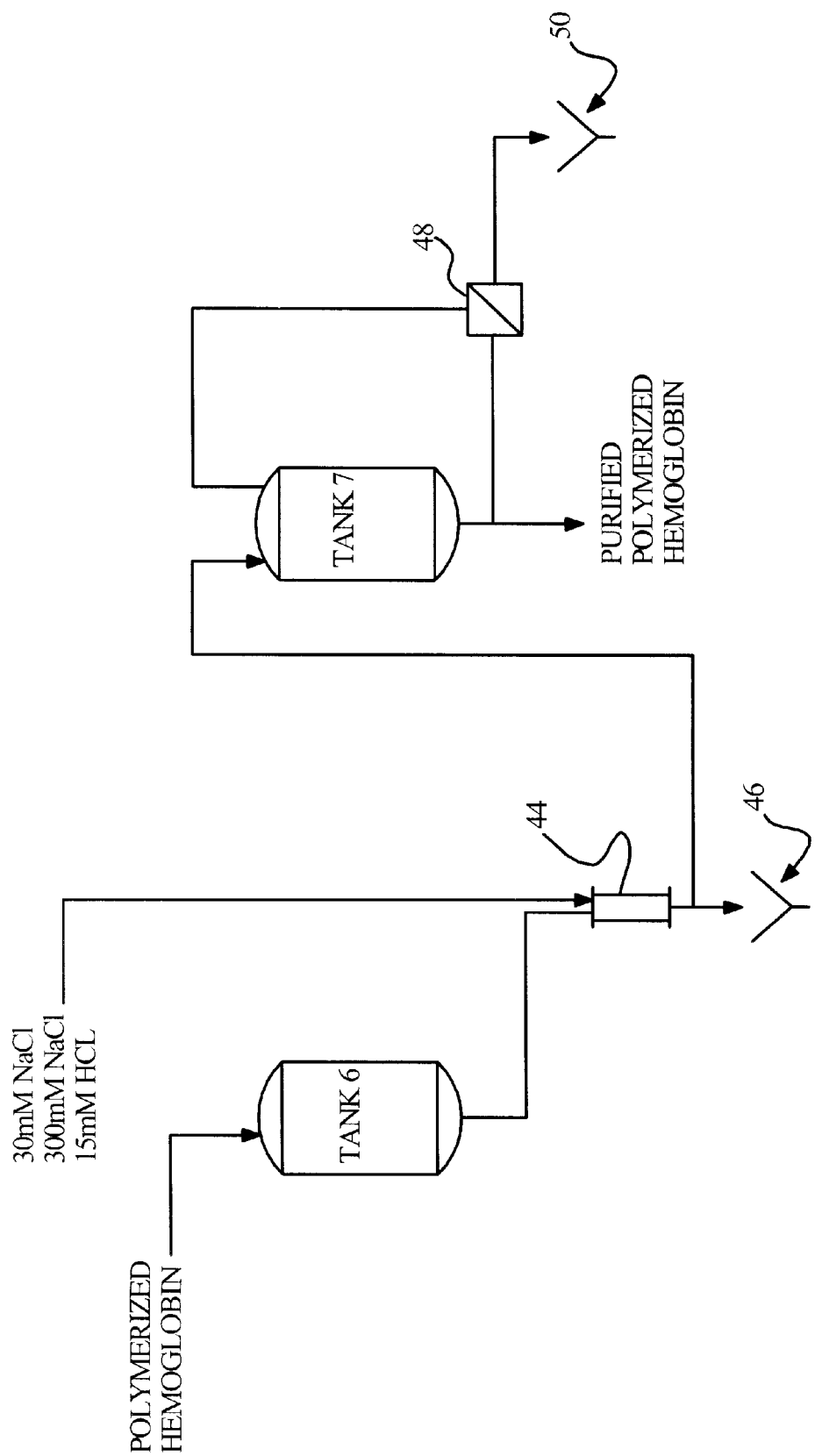
FIG. 5 is a schematic diagram depicting a column chromatography purification process employed in the invention.

In one embodiment, the solution is transferred to chromatography feed vessel, Tank 6, as shown in FIG. 5. In this embodiment, the resulting solution of oxyhemoglobin is then diluted to about 200 L (4% total hemoglobin) in Tank 6 and the concentration of chloride is adjusted to 22 mM with sodium chloride solution. No adjustment of sodium concentration is necessary.

Five 40 L aliquots of the resulting hemoglobin solution are then chromatographed using Column 44. Column 44 contains an affinity gel which is an agarose gel modified with a yellow dye (commercially available from Affinity Chromatography, Ltd., as Mimetic Yellow No. 1) having greater affinity for polymer than tetramer.

The chromatography is accomplished as follows. 40 L of oxygenated, polymerized, pyridoxylated, stroma-free hemoglobin solution is loaded onto Column 44. The column is washed with 15 column volumes (about 750 L) of 30 mM aqueous NaCl buffer to remove tetramer. The column is then washed with about 250 L of a 300 mM sodium chloride buffer to wash the polymer off. Polymer fractions are collected in Tank 7. Unwanted fractions are sent to drain 46. After each aliquot is removed, the column is regenerated with 15 mM HCL solution (150 L), reequilibrated with 30 mM equeous NaCl (250 L) and another aliquot of feed solution (40 L) is loaded to the column. The column is again washed with 30 mM NaCl followed by 300 mM NaCl. 40 L aliquots of hemoglobin solution are added to the column and chromatographed until Tank 6 is empty.

The collected fractions in Tank 7 are ultrafiltered (concentrated) using filter 48 associated with drain 50 to a volume of about 40 L (6% total hemoglobin). The concentrated hemoglobin solution is then transferred to gas exchange Tank 8 for deoxygenation.

Figure 6:
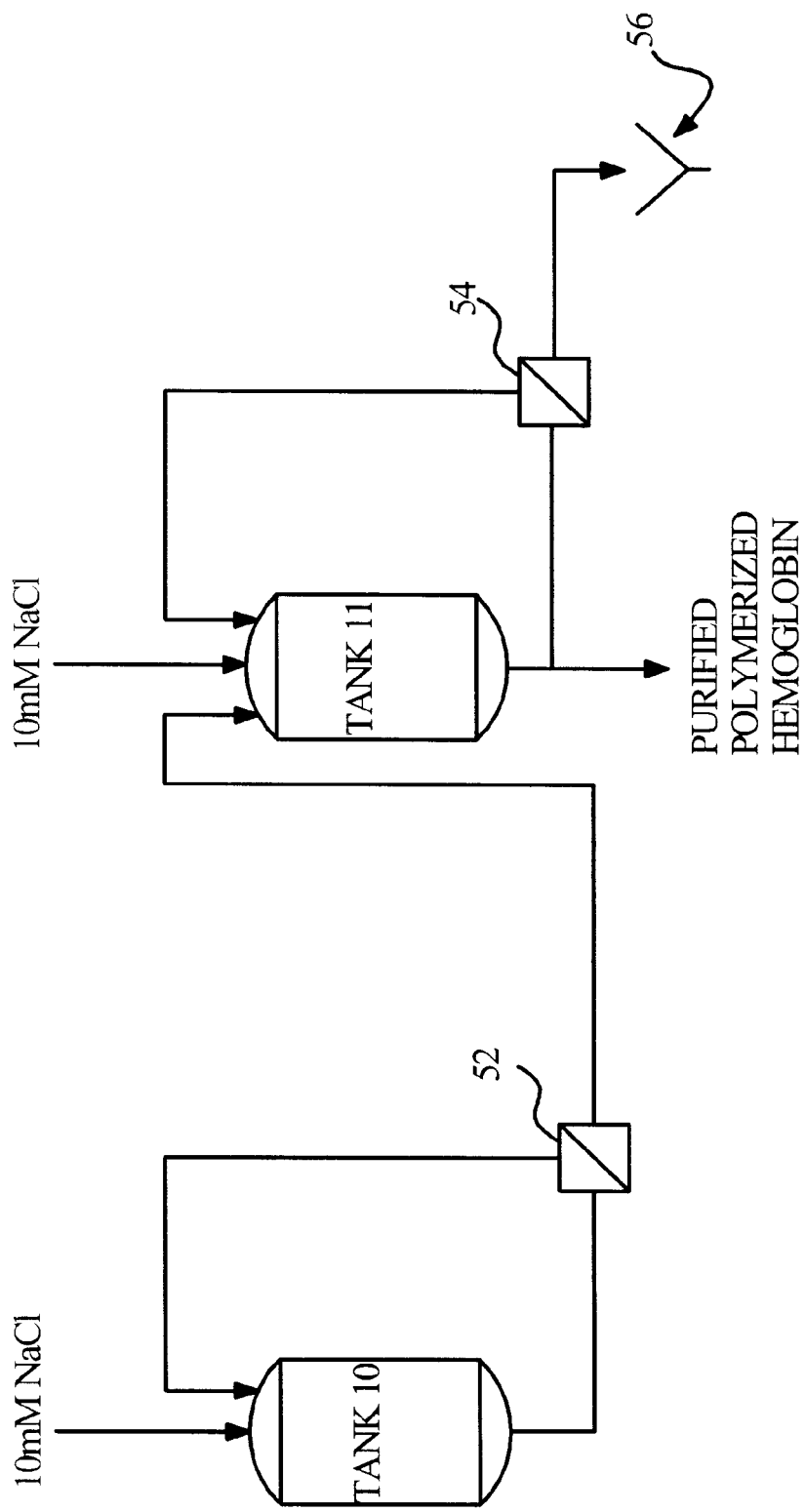
FIG. 6 is a schematic diagram depicting a membrane filtration purification process employed in the invention.

Alternatively, the solution is transferred to a filtration recycle vessel 10, as shown in FIG. 6. The hemoglobin is then diluted to about 4% THb in Tank 10. The 4% THb solution is then diafiltered using 10 mM NaCl and a 300,000 molecular weight filter 52 commercially available from Pall-Filtron. The filtration is continued until about 97% of the hemoglobin material passes through the filter and into Tank 11. (About 3% of the material, i.e., high molecular weight polymers is retained in Tank 10). The amount of hemoglobin is determined spectrophotometrically using a cooximeter.

The resulting material in Tank 11 is about 2–4% TH6 and contains about 7–10% tetramer based on THb. The 2–4% THb is then diafiltered using 10 mM NaCl and a 100,000 molecular weight filter 54 commercially available from Pall-Filtron associated with drain or trap 56. The filtration is continued until the level of tetramer, as determined by size exclusion chromatography using a BioSep SEC-S3000 600× 7.8 mm column is less than 0.8% of the hemoglobin mass by weight. The resulting purified hemoglobin solution remains initially in Tank 11 and is subsequently transferred to gas exchange Tank 8 for deoxygenation.

Gas exchange Tank 8 may be the same tank as Tank 4 or, preferably, a different tank. Gas exchange Tank 8 is equipped in essentially the same fashion as gas exchange Tank 4 in FIG. 1 and is attached to foam can 58 in a fashion identical to that of Tank 4 and foam can 36. Deoxygenation is accomplished in about 2.5 hours with a nitrogen sparge at about 10° C. and a solution pH of about 7.5. Nitrogen sparging is continued until less than about 16% oxyhemoglobin, based on the weight of total hemoglobin, remains in the solution. The resulting deoxyhemoglobin solution is subsequently transferred to Tank 9 for formulation.

In formulation Tank 9, the solution is first concentrated to about 7% total hemoglobin, and the pH adjusted to about 8.8 to 9.0 at 4° C. The pH is adjusted using 0.2 M NaOH. Electrolyte solutions are then added to the pH 8.8 to 9.0 hemoglobin solution. Glucose and glycine are added to achieve final concentrations of about 5 g/L and 1.75 g/L respectively. Potassium chloride is added to the solution to obtain a potassium concentration of about 3.5 to 4.5 mM. 3 M sodium chloride is then added to obtain a 85–110 mM chloride concentration. Sodium lactate is subsequently added to obtain a 135–155 mM concentration of sodium ion. Finally, a 0.45 molar ascorbic acid solution is added to raise the ascorbic acid concentration up to about 1000 mg/L. Ascorbic acid is added as a preservative/antioxidant for storage. The resulting hemoglobin solution has a final osmolality of about 280–360 mmole per kg.

The formulated hemoglobin solution is then concentrated to about 10% total hemoglobin using filter 60 associated with trap 62 and the 10% hemoglobin solution is then sterilized by filtration by filter 64 and aseptically filled into presterilized bags.

The characteristics of the product prepared in this example, Batch A, are shown in Table 1. In addition, the characteristics of Batches B and C, both prepared according to the procedure set forth above for Batch A, are shown in Table 1.

TABLE 1

| TEST | Batch A | Batch B | Batch C |
|---|---|---|---|
| Hemoglobin, g/dL | 10.4 | 10.2 | 10.2 |
| Methemoglobin, % | 4.6 | 6.0 | 5.6 |
| Carboxyhemoglobin, % | 0.2 | 1.4 | 1.5 |
| P50 (Torr, pH 7.35–7.45, pCO$_2$ 35–40 torr) | 28.5 | 26.8 | 27.0 |
| Osmolality, mmol/KG | 318 | 320 | 317 |
| Sodium, mmol/L | 142 | 144 | 142 |
| Potassium, mmol/L | 4.0 | 4.0 | 4.0 |
| Chloride, mmol/L | 98 | 99 | 94 |
| Free iron, ppm | 0.7 | 1.2 | 1.0 |
| Molecular Weight distribution, % at each MW (Kd) | 128:16 192:26 256[8]:58 | 128:11 192:23 256[8]:66 | 128:16 192:26 256[8]:58 |
| Tetramer, % | 0.4 | 0.3 | 0.4 |
| Endotoxin, EU/mL | <0.03 | <0.03 | <0.03 |

[8]Material also includes a small amount of higher molecular weight material.

In the foregoing, there has been provided a detailed description of preferred embodiments of the present invention for the purpose of illustration and not limtation. It is to be understood that all other modifications, ramifications and equivalents obvious to those having skill in the art based on this disclosure are intended to be within the scope of the invention as claimed.

What is claimed is:

1. An aqueous solution of pyridoxylated, polymerized hemoglobin comprising about 16% by weight based on the weight of total hemoglobin in the solution of hemoglobin polymer with a molecular weight of about 128 kd, about 26% by weight based on the weight of total hemoglobin in the solution of hemoglobin polymer with a molecular weight of about 192 kd, and about 58% by weight based on the weight of total hemoglobin in the solution of hemoglobin polymer with a molecular weight of about 256 kd.

2. A solution of hemoglobin according to claim 1, wherein the solution has a half-life in a human patient of about 15 hours.

3. A solution of hemoglobin according to claim 1, wherein the solution has a half-life in a human patient of about 24 hours.

4. A solution of hemoglobin according to claim 1, wherein the solution produces no appreciable decrease in kidney performance when infused into a human patient in an amount of up to about 5 liters.

5. A solution of hemoglobin according to claim 1, wherein the solution produces no appreciable decrease in kidney performance when infused into a human patient in an amount of up to about 5 liters, and the solution has a half-life in a human patient of about 24 hours.

6. A solution of hemoglobin according to claim 1, wherein the hemoglobin is a glutaraldehyde-polymerized hemoglobin.

7. A method for the treatment of a human patient in need of a transfusion, comprising administering to the patient up to about 1.5 liters of the pyridoxylated, polymerized hemoglobin solution of claim 1.

8. A method for the treatment of a human patient in need of a transfusion, comprising administering to the patient up to about 3.0 liters of the pyridoxylated, polymerized hemoglobin solution of claim 1.

9. A method for the treatment of a human patient in need of a transfusion, comprising administering to the patient up to about 5.0 liters of the pyridoxylated, polymerized hemoglobin solution of claim 1.

10. A method according to claim 9, wherein the hemoglobin is a glutaraldehyde-polymerized hemoglobin.

11. An aqueous solution of pyridoxylated, polymerized hemoglobin comprising:
   (a) a total hemoglobin of between 9.5 to 12.0 g/dl;
   (b) a total methemoglobin at less than 8% of the total hemoglobin;
   (c) a total carboxyhemoglobin at less than 5% of the total hemoglobin;
   (d) an oxygen-hemoglobin dissociation of between 23 to 32 torr;
   (e) an osmolality of between 280 to 360 mmol/Kg;
   (f) a sodium concentration of between 135 to 155 mmol/L;
   (g) a potassium concentration of between 3.5 to 4.5 mmol/L;
   (h) a chloride concentration of between 85 to 110 mmol/Kg;
   (i) a total free iron of less than 2.0 ppm;
   (j) a 128 Kd peak molecular weight distribution of between 10 and 24%;
   (k) a 192 Kd peak molecular weight distribution of between 18 and 30%;
   (l) a 256 Kd peak molecular weight distribution of between 45 and 70%;
   (m) a total tetramer of less than 0.8%;
   (n) endotoxin at less than 0.03 EU/ml;
   (o) phospholipids at less than 50 ng/Hb; and
   (p) glycolipids at less than 2 ng/Hb.

12. A solution according to claim 11, where the hemoglobin solution produces no appreciable decrease in kidney performance when infused into a human patient in an amount of up to about 1.5 liters.

13. A solution of pyridoxylated, polymerized hemoglobin comprising about 16% by weight based on the weight of total hemoglobin in the solution of hemoglobin polymer with a molecular weight of about 128 kd, about 26% by weight based on the weight of total hemoglobin in the solution of hemoglobin polymer with a molecular weight of about 192 kd, and about 58% by weight based on the weight of total hemoglobin in the solution of hemoglobin polymer with a molecular weight of about 256 kd that produces no appreciable decrease in kidney performance when infused into a human patient in an amount of up to about 3 liters, obtainable by a process comprising the steps of:
   (a) passing outdated blood or non-outdated blood through a suitable aspiration device at reduced pressure to produce aspirated blood;
   (b) removing leucocytes from the aspirated blood by filtering aspirated blood through a series of filters having a minimum average pore size sufficient to prevent the passage of leucocytes to produce a filtered solution;
   (c) washing the filtered product of (b) in a 1% sodium chloride solution under a carbon monoxide atmosphere to produce a washed solution with a pH of about 6.0 to about 6.5;
   (d) diluting the washed solution of (c) with water to form a solution of lysed cells;
   (e) filtering the solution of lysed cells across a filter to produce a hemoglobin solution free from stroma contaminants and cell wall material;
   (f) heating and filtering the hemoglobin solution of (e) to a temperature of about 60–62° C. for about 10 hours to yield a heat-treated stroma-free hemoglobin solutions;
   (g) concentrating and diafiltering the heat-treated stroma-free hemoglobin solution yielding a carboxy hemoglobin solution;
   (h) degassing the carboxy hemoglobin solution by sparging oxygen and then nitrogen through the heat-treated solution at a temperature of about 10° C. to produce a foam to yield a degassed, heat-treated hemoglobin solution;
   (i) pyridoxylating the degassed solution using pyridoxal-5"-phosphate at a molar ratio of pyridoxal-5"-phosphate to hemoglobin of about 1:1 to 3:1 to yield a solution of pyridoxylated hemoglobin;
   (j) polymerizing the solution of pyridoxylated hemoglobin using an aqueous glutaraldehyde solution to produce a solution of pyridoxylated, polymerized hemoglobin containing about 65–75% polymer tetramer;
   (k) oxygenating and diluting the polymerized solution until the solution contains about 4% by weight hemoglobin;
   (l) purifying the solution of (k to remove tetrameric hemoglobin and collecting purified pyridoxylated, polymerized hemoglobin, where the solution contains less than 0.8% based on the total weight of hemoglobin of tetramer;
   (m) deoxygenating the purified pyridoxylated, polymerized hemoglobin with nitrogen;
   (n) adjusting the pH and electrolyte levels in the solution of purified pyridoxylated, polymerized hemoglobin to physiological levels;
   (o) concentrating and sterilizing the pH adjusted solution in (n); and
   (p) thereby obtaining the solution of pyridoxylated, polymerized hemoglobin.

14. A process for preparing a solution of pyridoxylated, polymerized hemoglobin comprising about 16% by weight based on the weight of total hemoglobin in the solution of hemoglobin polymer with a molecular weight of about 128 kd, about 26% by weight based on the weight of total hemoglobin in the solution of hemoglobin polymer with a molecular weight of about 192 kd, and about 58% by weight based on the weight of total hemoglobin in the solution of hemoglobin polymer with a molecular weight of about 256 kd that produces no appreciable decrease in kidney performance when infused into a human patient in an amount of up to about 3 liters, said process comprising the steps of:
   (a) removing leucocytes by filtering a mixture containing red blood cells through a filter having a minimum average pore size sufficient to prevent the passage of leucocytes to produce a filtered product;

(b) lysing the red blood cells in the filtered product;

(c) adding carbon monoxide and heating the product of (b) to a temperature of about 60–62° C. for about 10 hours to yield a heat-treated hemoglobin solution;

(d) filtering the heat treated hemoglobin solution to remove stroma and stromal contaminants precipitated by the heating;

(e) degassing the heat-treated hemoglobin solution by sparging oxygen and then nitrogen through the heat-treated solution at a temperature of about 10° C. to produce a foam to yield a degassed, heat-treated hemoglobin solution;

(f) pyridoxylating the degassed solution to yield a solution of pyridoxylated hemoglobin;

(g) polymerizing the solution of pyridoxylated hemoglobin to produce a solution of pyridoxylated, polymerized hemoglobin;

(h) oxygenating the pyridoxylated polymerized hemoglobin solution to produce an oxygenated solution;

(i) purifying the oxygenated solution to remove tetrameric hemoglobin and collecting purified pyridoxylated, polymerized hemoglobin, where the solution contains less than 0.8% based on the total weight of hemoglobin of tetramer;

(j) deoxygenating the purified oxygenated pyridoxylated, polymerized hemoglobin; and (k) adjusting the pH and electrolyte levels in the solution of purified deoxygenated pyridoxylated, polymerized hemoglobin to physiological levels.

15. A process according to claim 14, wherein the degassed solution is pyridoxylated by contacting the degassed solution with pyridoxal-5-phospate at a molar ratio of pyridoxal-5-phosphate to hemoglobin of about 2:1.

16. A process according to claim 14, wherein the degassed solution is pyridoxylated by contacting the degassed solution with pyridoxal-5-phospate at a molar ratio of pyridoxal-5-phosphate to hemoglobin of from about 1:1 to 3:1.

17. A process according to claim 16, wherein the pyridoxal-5-phospate is contacted with the hemoglobin and borohydride for about one hour.

18. A process according to claim 17, wherein the hemoglobin in the pyridoxylated solution is polymerized by contacting the pyridoxalated solution with glutaraldehyde at a glutaraldehyde to hemoglobin molar ratio of from about 24:1.

19. A process according to claim 18, wherein the pyridoxylated solution is contacted with glutaraldehyde for about 18 hours and then quenched.

20. A process for preparing a solution of pyridoxylated, polymerized hemoglobin comprising about 16% by weight based on the weight of total hemoglobin in the solution of hemoglobin polymer with a molecular weight of about 128 kd, about 26% by weight based on the weight of total hemoglobin in the solution of hemoglobin polymer with a molecular weight of about 192 kd, and about 58% by weight based on the weight of total hemoglobin in the solution of hemoglobin polymer with a molecular weight of about 256 kd that produces no appreciable decrease in kidney performance when infused into a human patient in an amount of up to about 3 liters, said process comprising the steps of:

(a) passing outdated blood or non-outdated blood through a suitable aspiration device at reduced pressure to produce aspirated blood;

(b) removing leucocytes from the aspirated blood by filtering the aspirated blood through a series of filters having a minimum average pore size sufficient to prevent the passage of leucocytes to produce a filtered solution;

(c) washing the filtered product of (b) in a 1% sodium chloride solution under a carbon monoxide atmosphere to produce a washed solution with a pH of about 6.0 to about 6.5;

(d) diluting the washed solution of (c) with water to form a solution of lysed cells;

(e) filtering the solution of lysed cells across a filter to produce a hemoglobin solution free from stroma contaminants and cell wall material;

(f) heating and filtering the hemoglobin solution of (e) to a temperature of about 60–62° C. for about 10 hours to yield a heat-treated stroma-free hemoglobin solution;

(g) concentrating and diafiltering the heat-treated stroma-free hemoglobin solution yielding a carboxy hemoglobin solution;

(h) degassing the carboxy hemoglobin solution by sparging oxygen and then nitrogen through the heat-treated solution at a temperature of about 10° C. to produce a foam to yield a degassed, heat-treated hemoglobin solution;

(i) pyridoxylating the degassed solution using pyridoxal-5"-phosphate at a molar ratio of pyridoxal-5"-phosphate to hemoglobin of about 1:1 to 3:1 to yield a solution of pyridoxylated hemoglobin;

(j) polymerizing the solution of pyridoxylated hemoglobin using an aqueous glutaraldehyde solution to produce a solution of pyridoxylated, polymerized hemoglobin containing of about 65–75% polymer;

(k) oxygenating and diluting the polymerized solution until the solution contains about 4% by weight hemoglobin;

(l) purifying the solution of (k) to remove tetrameric hemoglobin and collecting purified pyridoxylated, polymerized hemoglobin, where the solution contains less than 0.8% based on the total weight of hemoglobin of tetramer;

(m) deoxygenating the purified pyridoxylated, polymerized hemoglobin with nitrogen;

(n) adjusting the pH and electrolyte levels in the solution of purified pyridoxylated, polymerized hemoglobin to physiological levels;

(o) concentrating and sterilizing the pH adjusted solution in (n); and (p) thereby obtaining the solution of pyridoxylated, polymerized hemoglobin.

* * * * *